(12) United States Patent
Walia

(10) Patent No.: US 7,939,286 B2
(45) Date of Patent: May 10, 2011

(54) ENHANCING A LUMINESCENT SIGNAL

(75) Inventor: Rampyari R. Walia, Alpine, CA (US)

(73) Assignee: Targeting Systems, El Cajon, CA (US)

(*) Notice: Subject to any disclaimer, the term of this patent is extended or adjusted under 35 U.S.C. 154(b) by 451 days.

(21) Appl. No.: 11/885,713

(22) PCT Filed: Mar. 7, 2006

(86) PCT No.: PCT/US2006/008141
§ 371 (c)(1),
(2), (4) Date: Apr. 2, 2008

(87) PCT Pub. No.: WO2006/096735
PCT Pub. Date: Sep. 14, 2006

(65) Prior Publication Data
US 2008/0274485 A1    Nov. 6, 2008

Related U.S. Application Data

(60) Provisional application No. 60/659,152, filed on Mar. 7, 2005.

(51) Int. Cl.
*C12Q 1/66* (2006.01)
(52) U.S. Cl. ............................................. 435/8
(58) Field of Classification Search ................ 435/8
See application file for complete search history.

(56) References Cited

U.S. PATENT DOCUMENTS

| 5,292,658 | A | 3/1994 | Cormier et al. |
| 5,641,641 | A | 6/1997 | Wood |
| 5,744,320 | A | 4/1998 | Sherf et al. |
| 6,171,809 | B1 * | 1/2001 | Roelant ............................ 435/8 |
| 6,232,107 | B1 | 5/2001 | Bryan et al. |

OTHER PUBLICATIONS

Cormier et al., J. Cell. Physiol. 81: 291-298(1973).
Smart, et al. Biol. Proced. Online, 7(1): 1-7 (2005).
Shimomura, et al. Biol. Bull. 201:339-347 (2001).
Tannous et al. Mol. Therap. 11(3):435-43 (2005).
Targeting Systems "Gaussia Luciferase Assay System" online: 1-7 (2005).
Verhaegen, et al. Anal. Chem., 74:4378-4385 (2002).

* cited by examiner

*Primary Examiner* — Tekchand Saidha
(74) *Attorney, Agent, or Firm* — Morgan Lewis & Bockius, LLP

(57) ABSTRACT

Methods and compositions are described for assaying luciferase bioluminescence in vitro and in vivo cells. The compositions provide at least one of enhanced stability of signal or magnitude of signal by varying the composition of the buffer. One or more of the following parameters have been varied: the presence or absence of EDTA, the concentration of NaCl, the concentration of coelenterazine, the evaluation of ionic and non-ionic detergent, the amount of detergent, how the detergent has been added and the time over which the signal has been recorded. Also disclosed are dual reporter systems.

24 Claims, 10 Drawing Sheets

ENHANCING A LUMINESCENT SIGNAL

CROSS REFERENCE

This application is a §371 application of international application number PCT/US2006/008141 filed on Mar. 7, 2006, which claims priority from U.S. provisional application No. 60/659,152 filed on Mar. 7, 2005, herein incorporated by reference.

BACKGROUND

Luciferases are enzymes that catalyze reactions that emit light. Luciferases are named according to their source organisms such as beetles (firefly) (see for example U.S. Pat. No. 5,641,641) or marine organisms. Examples of bioluminescent marine animals include: *Renilla*, also known as sea pansies, which belong to a class of coelenterates known as the anthozoans. In addition to *Renilla*, other representative bioluminescent genera of the class Anthozoa include *Cavarnularia, Ptilosarcus, Stylatula, Acanthoptilum*, and *Parazoanthus*. All of these organisms are bioluminescent and emit light as a result of the action of an enzyme (luciferase) on a substrate (luciferin) under appropriate biological conditions. Prior studies have demonstrated that all of the above-mentioned anthozoans contain similar luciferases and luciferins. See, for example, Cormier et al., *J. Cell. Physiol.* 81: 291-298 (1973). The luciferases and luciferins from each of these anthozoans will cross-react with one another to produce the characteristic blue luminescence observed in *Renilla* extracts. Each of these luciferases has similar biochemical properties, and the biochemical requirements for bioluminescence were reported to be identical (U.S. Pat. No. 5,292,658) regardless of the anthozoan from which the luciferase was derived.

Different luciferases have different properties with regard to substrate specificity and intensity of light emission and stability of the bioluminescent signal, which is commonly measured by a luminometer. Luciferases are useful as transcriptional reporter genes and in imaging reporter gene expression in living subjects and many other applications in molecular biology.

Luciferases that utilize coelenterazine luciferin as a substrate generate a flash of bioluminescence of a magnitude that can be useful for certain molecular biology reactions such as high through-put screening. This use among others would benefit from the extension of the time period of the bioluminescent signal.

SUMMARY

In an embodiment of the invention, a luciferase assay buffer is provided that contains coelenterazine substrate, sodium chloride at a concentration less than in physiological saline, and a detergent, the assay buffer being suitable for detecting bioluminescence from a coelenterazine-dependent luciferase for a time period of greater than about 30 seconds to about 1 minute where for example, bioluminescence from *Gaussia* luciferase can be detected in a luminometer over a time period of at least about 30 seconds from addition of the assay buffer to the luciferase. Bioluminescence can be additionally detected from *Renilla* luciferase over a time period of at least one minute from adding the assay buffer. The assay buffer may be incorporated in a kit with instructions for its use.

In an example of the assay buffer above, the sodium chloride has a concentration in the range of about 0.01-0.15M, preferably does not contain calcium or magnesium ions and optionally contains EDTA at a concentration of no more than about 3%. The assay buffer may further contain a non-ionic detergent at a concentration in the range of about 0.001%-0.5%. Examples of detergents that may be used in the buffer include Igepal CA-650 (NP40), Triton X-100, Tween8O and deoxycholate (DOC).

In a further embodiment of the invention, the luciferase assay buffer contains coelenterazine at a concentration of no greater than about 5 µM.

In a further embodiment of the invention, a luciferase assay buffer is provided in which the salt concentration is in the range of about 0.01-0.15M, the coelenterazine is at a concentration of less than 5 µM and the buffer further contains a non-ionic detergent at a concentration in the range of about 0.001%-0.5%. The assay buffer may be incorporated into a kit with instructions for its use.

In a further embodiment of the invention, a luciferase assay buffer is provided in which the coelenterazine concentration is about 1 µM-5 µM, the non-ionic detergent is at a concentration of at least about 0.05% and the buffer further comprises EDTA, wherein the assay buffer is capable of stabilizing the bioluminescent emission of *Gaussia* luciferase over a time period of at least 2 minutes. The method of using this buffer includes selecting this buffer and adding it to the luciferase.

In a further embodiment of the invention, a luciferase assay buffer is provided in which the non-ionic detergent has a concentration of less than about 0.05%, the assay buffer being capable of enhancing the magnitude of bioluminescence for *Gaussia* luciferase for a time period of at least about 30 seconds in the absence of EDTA. The method of using this buffer includes selecting this buffer and adding it to the luciferase. In an example of this method, a coelenterazine concentration of 4 µM is selected.

In a further embodiment of the invention, a method is provided for measuring a first and second luciferase in a single preparation where the method includes the following steps: (a) preparing a first assay buffer containing benzyl coelenterazine and a second buffer containing coelenterazine; (b) adding the benzyl coelenterazine to the cell preparation to measure an amount of bioluminescence from the first luciferase; (c) adding the coelenterazine to measure an amount of the first and second luciferase; and (d) calculating the difference in bioluminescence between (b) and (c) to determine the amount of the bioluminescence from the second luciferase. An example of the first luciferase is *Renilla* luciferase and the second luciferase is *Gaussia* luciferase.

In a further embodiment of the invention, a method for direct detection of cells transformed with a gene encoding *Gaussia* luciferase is provided in which an assay buffer described above is added to the cells in a culture medium and bioluminescence is detected by the naked eye or microscopy. Additionally, cells may be co-transfected with a plasmid expressing *Gaussia* luciferase fused with a gene encoding a target protein and a gene encoding an siRNA directed against the target protein. This is useful for screening a variety of siRNAs for gene silencing.

BRIEF DESCRIPTION OF THE DRAWINGS

FIG. 2 shows the effect of 0.02% v/v NP40, 0.02% v/v Triton X-100, 0.2% v/v DOC, 0.2% v/v Tween80 and 0.02% w/v sodium dodecyl sulfate (SDS) in an assay buffer that contains 0.5×PBS and 1.3 μM coelenterazine on the activity of *Gaussia* luciferase secreted from mammalian cells. The first four bars in each set indicate luciferase activity at time zero and the next three bars indicate the luciferase activity in the same tubes after 15 minutes.

Figure 3:
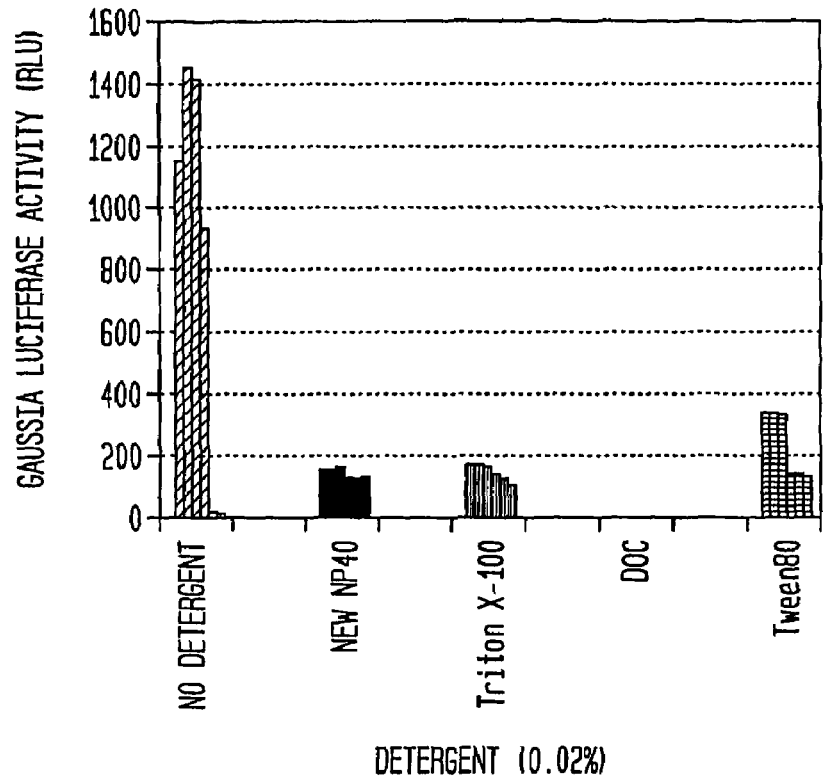

FIG. 3 shows the effect of 0.2% v/v of NP40, Triton X-100, DOC, and Tween δO in an assay buffer that contains 0.5×PBS and 1.3 μM coelenterazine on mammalian-secreted *Gaussia* luciferase activity. The first three bars in each set indicate *Gaussia* luciferase activity at time zero and the next three bars indicate the luciferase activity in the same tubes after 15 minutes.

Figure 4A:
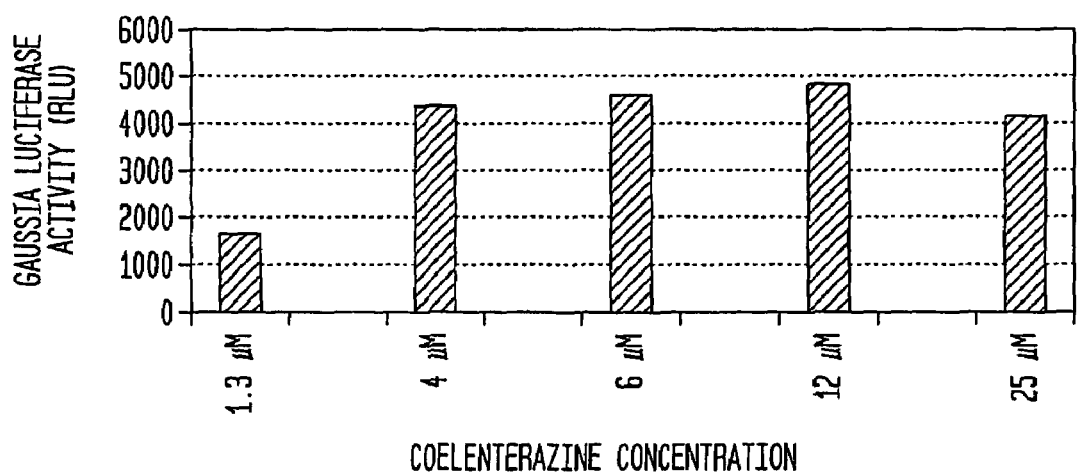

FIG. 4A shows the effect of varying coelenterazine concentrations (1.3 μM, 4 μM, 6 μM, 12 μM and 25 μM) in an assay buffer containing 0.5×PBS, 1% EDTA and 0.025% NP40 on mammalian-secreted *Gaussia* luciferase activity at zero time. The results show no significant increase in luciferase activity at concentrations greater than 4 μM of coelenterazine.

Figure 4B:
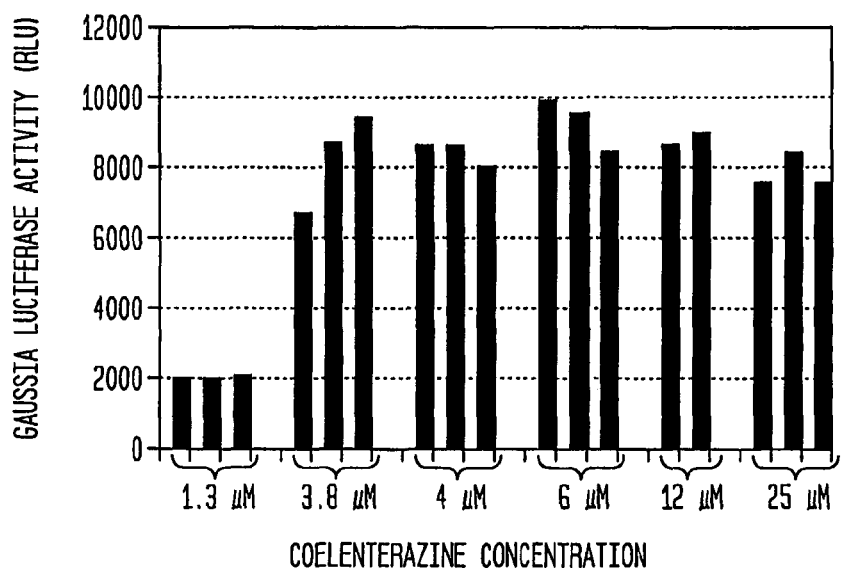

FIG. 4B shows the effect of varying coelenterazine concentration (1.3 μM, 3.8 μM, 4 μM, 6 μM, 12 μM and 25 μM) on the stability of recombinant bacterial luciferase. The results for triplicate samples are provided for each concentration of coelenterazine tested. The results show that no significant increases in luciferase activity occurs at concentrations greater than 4 μM of coelenterazine.

Figure 5:
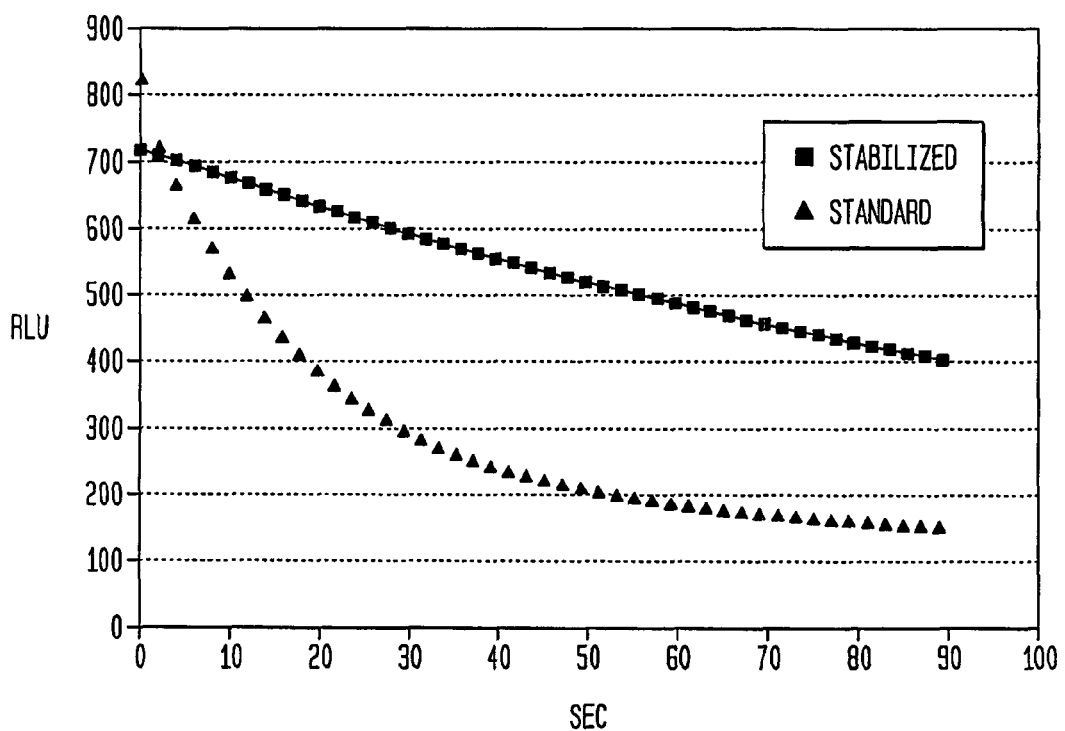

FIG. 5 shows a comparison of the *Gaussia* stabilized assay reagent (0.4×PBS, 1% EDTA, 0.025% NP40) compared with standard Promega *Renilla* assay reagent (Promega, Madison, Wis.) over a time period from 0-100 seconds for mammalian-secreted *Gaussia* luciferase.

Figure 6:
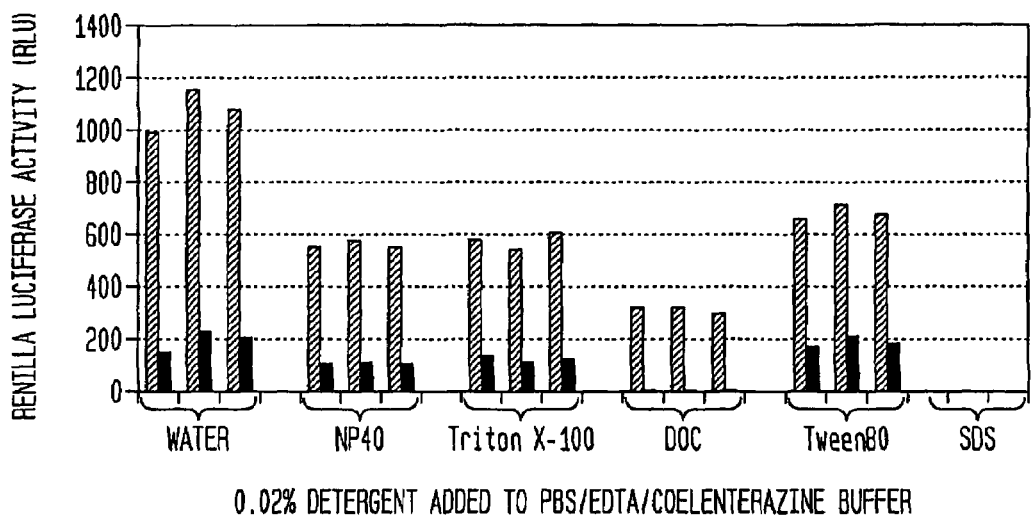

FIG. 6 shows the stabilizing effect of 0.02% v/v detergent (SDS is w/v) on *Renilla* luciferase activity. The results for triplicate samples at two time points are provided for each detergent tested. The time points in minutes are T=O and T=7. The detergents tested were NP40, Triton X, DOC, TweenδO and SDS with a control of water. In all samples, there was a significant loss of signal at the second time point.

Figure 7:
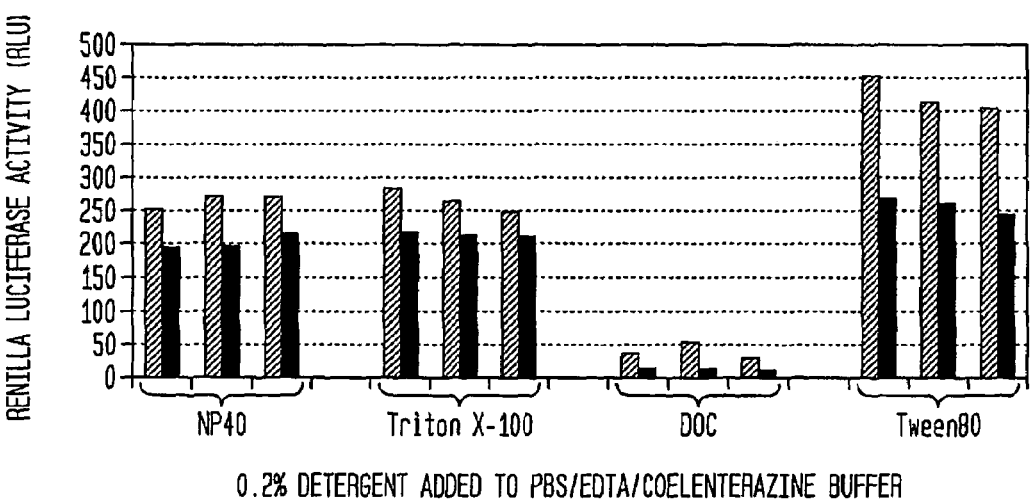

FIG. 7 shows the stabilizing effect of 0.2% v/v detergent (SDS is w/v) on *Renilla* luciferase activity. The results for triplicate samples at two time points are provided for each detergent tested. The time points in minutes are T=O and T=18. The detergents tested were NP40, Triton X, DOC, TweenδO and SDS with a control of water with NP40, Triton X-IOO and TweenδO showing a stabilizing effect at 0.2% concentration.

Figure 8:
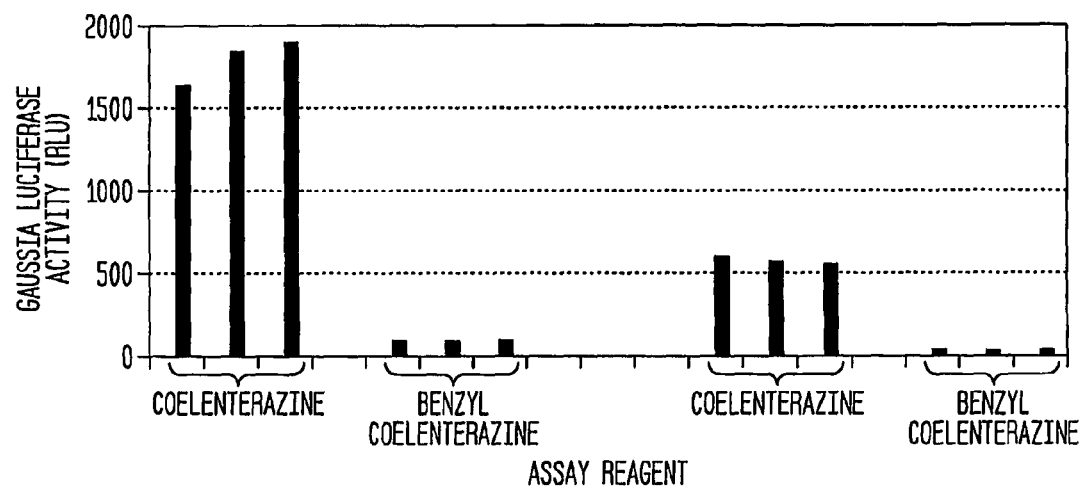

FIG. 8 shows the results of using 1.3 μM benzyl coelenterazine as a substrate compared with 1.3 μM coelenterazine in a buffer reagent also containing 0.5×PBS and 1% EDTA (w/v) and 0.025% NP40 for measuring the magnitude of bioluminescence from purified recombinant bacterial luciferase (right) or secreted mammalian luciferase (left). The results show that benzyl coelenterazine is a poor substrate for *Gaussia* luciferase.

Figure 9:
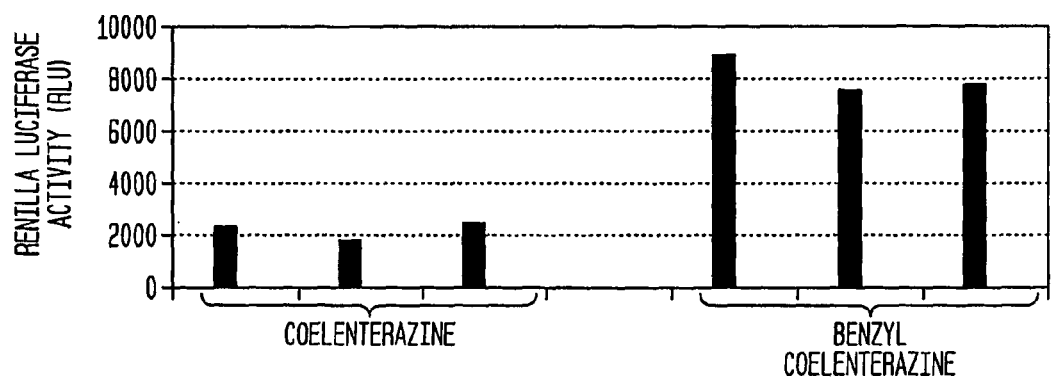

FIG. 9 shows the results of using 1.3 μM benzyl coelenterazine as a substrate compared with 1.3 μM coelenterazine in a buffer reagent also containing 0.5×PBS, 0.025% NP40 (v/v) and 1% EDTA (w/v) for measuring the amount and stability of bioluminescence from *Renilla* luciferase. The results show that benzyl coelenterazine is a good substrate for *Renilla* luciferase resulting in a significantly greater signal than observed for coelenterazine.

Figure 10:
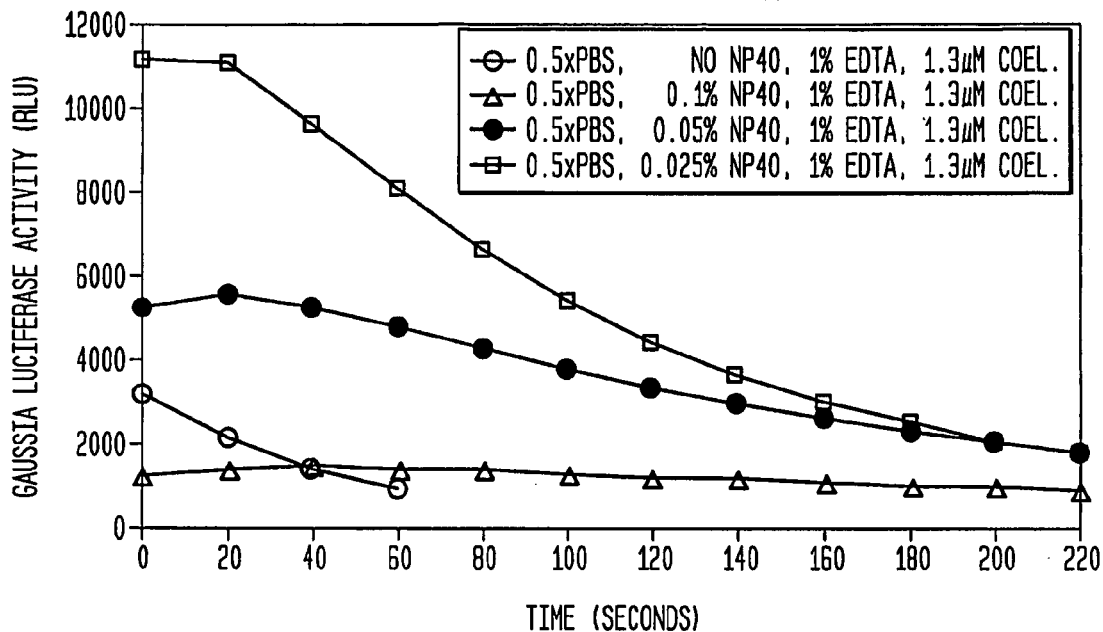

FIG. 10 shows the effect of varying the percentage of NP40 on the activity of secreted mammalian *Gaussia* luciferase activity using 1.3 μM coelenterazine. An increased magnitude of luminescent signal occurs with a reduced percentage of detergent up to 180 seconds. However, the stability profile of the bioluminescent signal improves with an increase in detergent concentration up to 220 seconds for 0.1% NP40.

Figure 11:
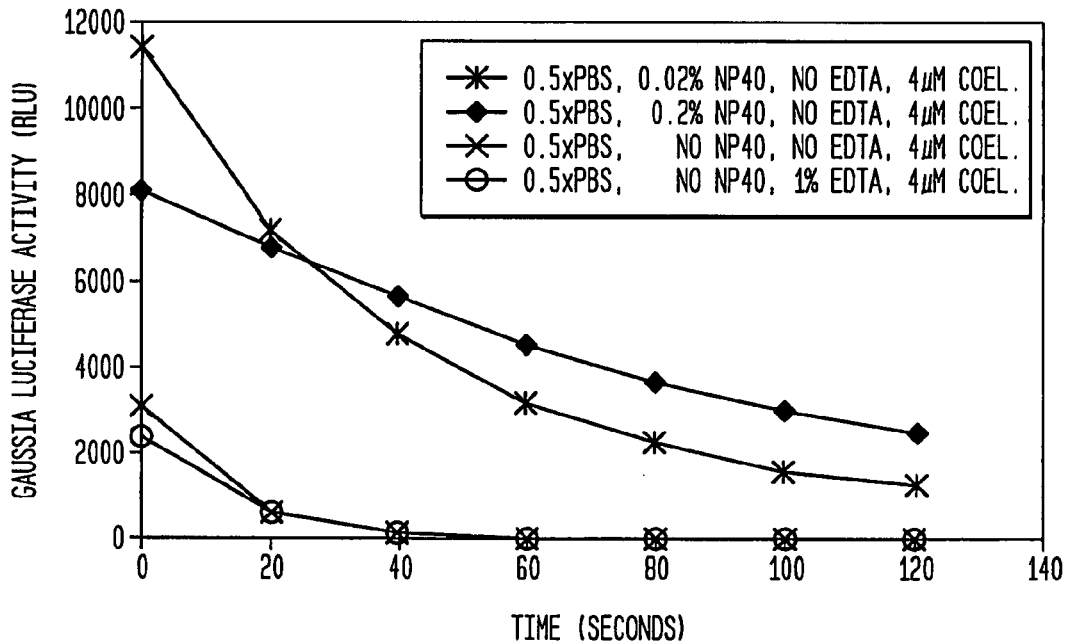

FIG. 11 shows the effect on bioluminescence from *Gaussia* luciferase over a 120 second time period using secreted luciferase from mammalian cells in an assay buffer consisting of 0.5×PBS, +/−1% EDTA w/v, 0.02% or 0.2% v/v NP40 and 4 μM coelenterazine. The greatest enhancement of magnitude of signal at time=zero was observed using 0.5×PBS, no EDTA, 0.02% NP40 and 4 μM coelenterazine. The most stable signal was observed in the preferred buffer of 0.2% NP40, 0.5×PBS, no EDTA and 4 μM coelenterazine.

Figure 12:
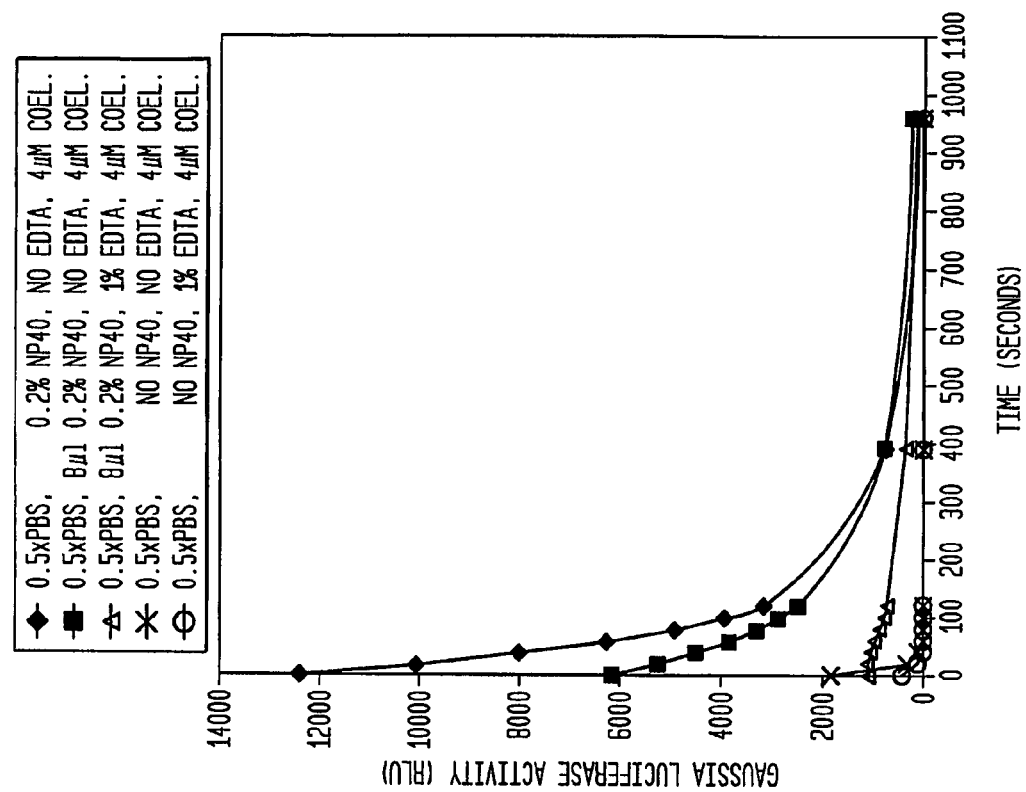

FIG. 12 shows the effect on bioluminescence from *Gaussia* luciferase over a 120 second time period using secreted luciferase from mammalian cells in an assay buffer consisting of 0.5×PBS, +/−1% EDTA and 0.2% NP40. In two samples (■, ▲), detergent was added to the luciferase before 4 μM coelenterazine was added and in the one sample (4-), the detergent was added directly to 4 μM coelenterazine. The greatest enhancement of magnitude of signal at time=zero was observed using 0.5×PBS, no EDTA, 0.2% NP40 and 4 μM coelenterazine. The most stable profile was achieved with 0.2% NP40 added prior to 4 μM coelenterazine, 0.5×PBS and 1% EDTA.

Figure 13:
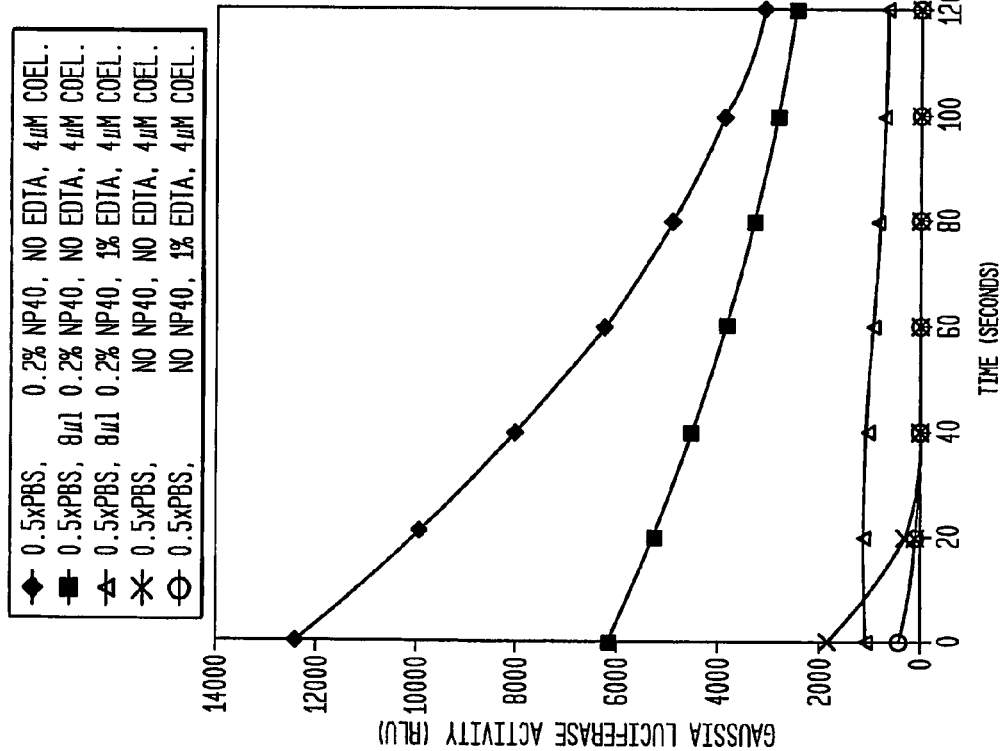

FIG. 13 shows the effect on bioluminescence over about 1000 seconds. The *Gaussia* luciferase was secreted from mammalian cells. 4 μM coelenterazine and 0.5×PBS were used throughout. Different samples contained or omitted 1% EDTA and 0.2% NP40. The most stable profile occurred using 0.5×PBS, 1% EDTA, and 0.2% NP40 added to the luciferase before the coelenterazine/PBS buffer.

Figure 14:
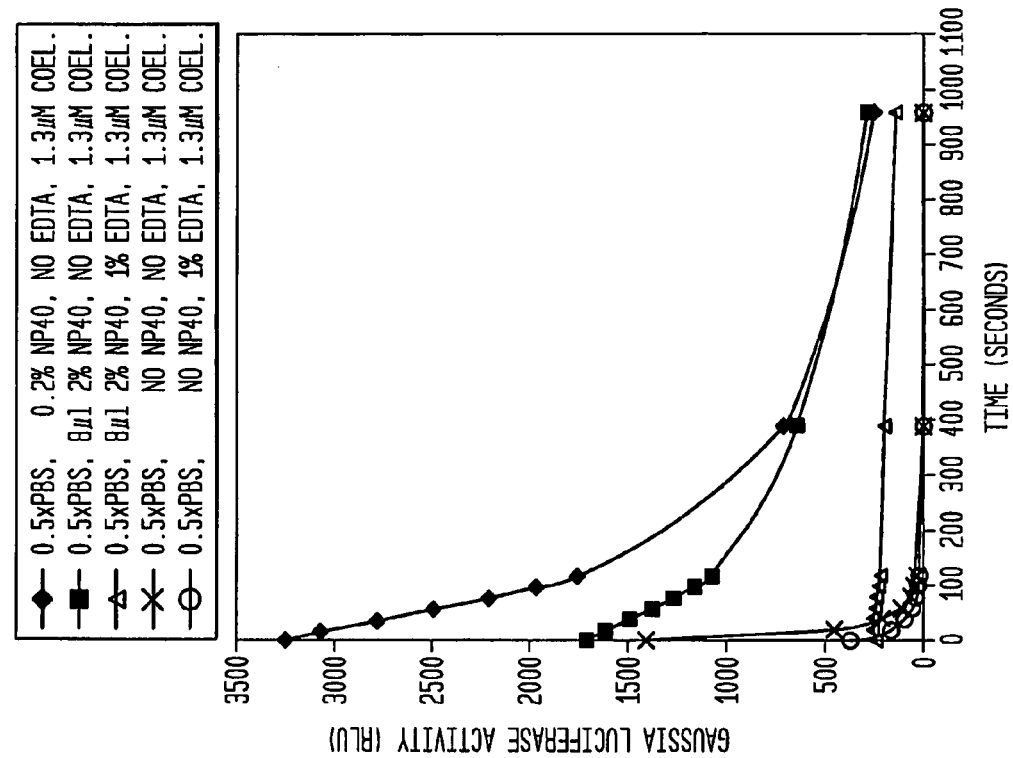

FIG. 14 shows the effect on bioluminescence from *Gaussia* luciferase over a 120 second time period using secreted luciferase from mammalian cells in an assay buffer consisting of 0.5×PBS, +/−1% EDTA and 0.2% NP40. The detergent was added to the luciferase before 1.3 μM coelenterazine was added in two samples (■, Δ). Alternatively, the detergent was added directly to 1.3 μM coelenterazine (4-). The greatest enhancement of magnitude of signal at time=zero was observed using 0.5×PBS, no EDTA, 0.2% NP40 and 1.3 μM coelenterazine. The most stable profile was achieved with 0.2% NP40 added prior to 1.3 μM coelenterazine, 0.5×PBS and 1% EDTA.

Figure 15:
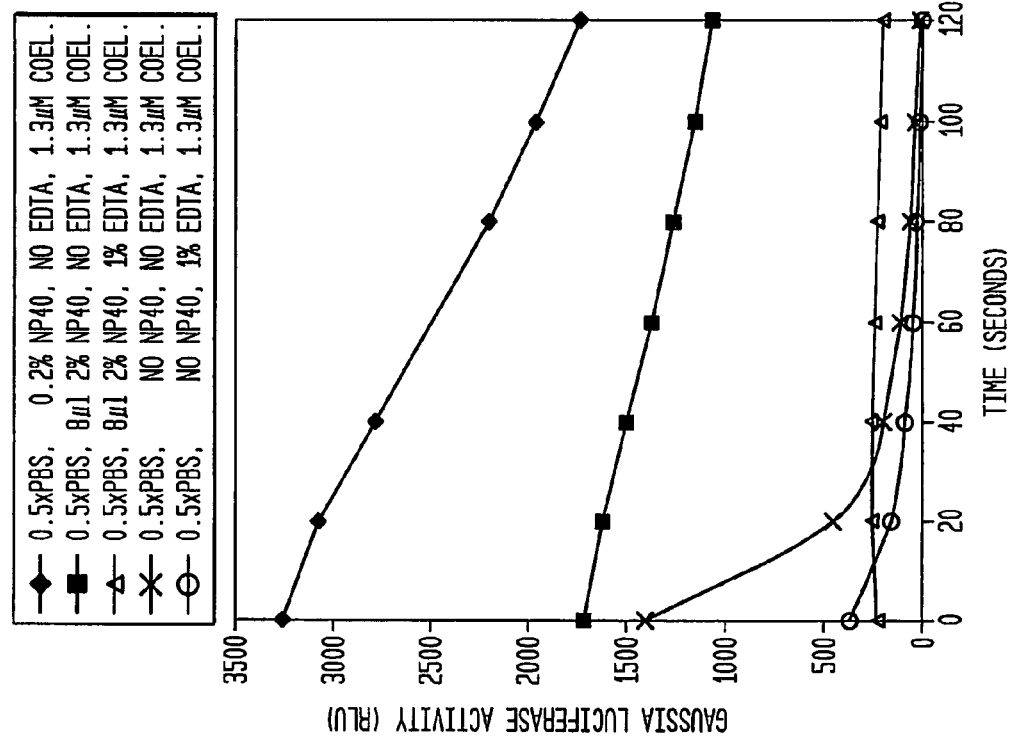

FIG. 15 shows the effect on bioluminescence over about 1000 seconds. The *Gaussia* luciferase was secreted from mammalian cells. 1.3 μM coelenterazine and 0.5×PBS were used throughout. Different samples contained or omitted 1% EDTA and 0.2% NP40. The half life of the luminescence using 0.5×PBS, 1% EDTA, 1.3 μM coelenterazine and 0.2% NP40 added to the luciferase before the coelenterazine/PBS buffer is greater than 18 minutes makes this particularly useful for high through-put screening.

Figure 16:
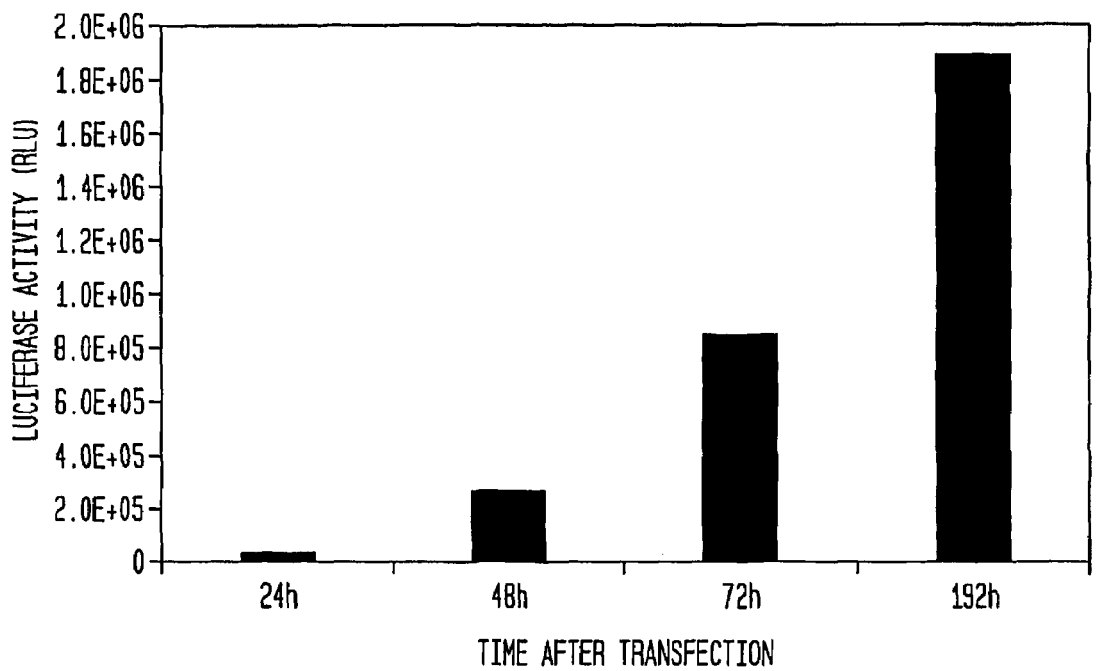

FIG. 16 shows the increase of secreted luciferase in the culture medium of transfected mammalian cells (HEK-293 cells) over 8 days. HEK-293 cells were transfected with expression vectors expressing *Gaussia* luciferase or a secreted gene. At the indicated time intervals, T=24, 48, 72 and 92 hours, 20 μl aliquots of the cell supernatants were assayed for luciferase activity by mixing each 20 μl sample with 50 μl of the assay buffer composition (0.4×PBS, 1% EDTA, 0.025% NP40, 1.3 μM coelenterazine). Data represents an average of quadruplicate determinations.

Figure 17:
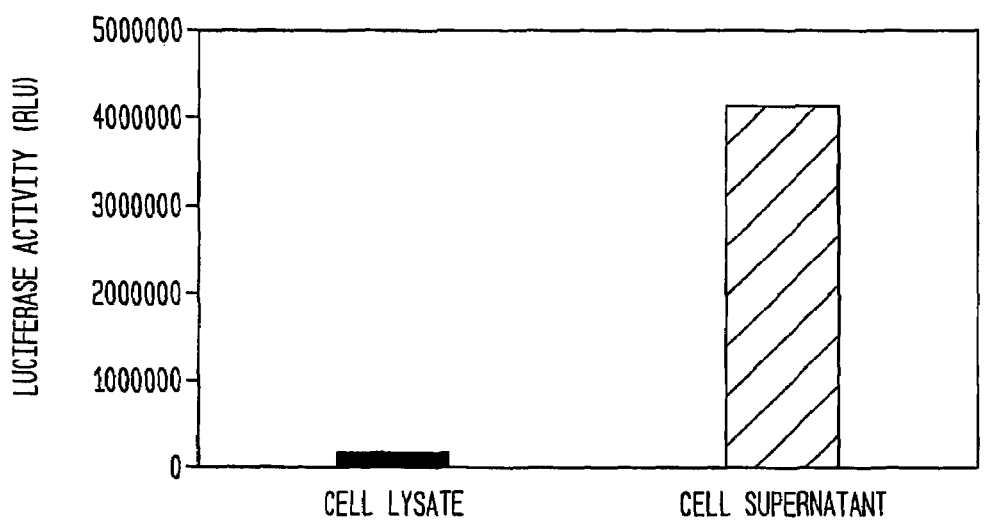

FIG. 17 shows a histogram comparing luciferase activity in the supernatant of a mammalian culture using *Gaussia* luciferase. The data is represented by a mean of triplicate determinations and shows total luciferase activity in cell lysate or supernatant 16 hr post transfection revealing only 3.8% of total activity that is cell-associated.

Figure 18:
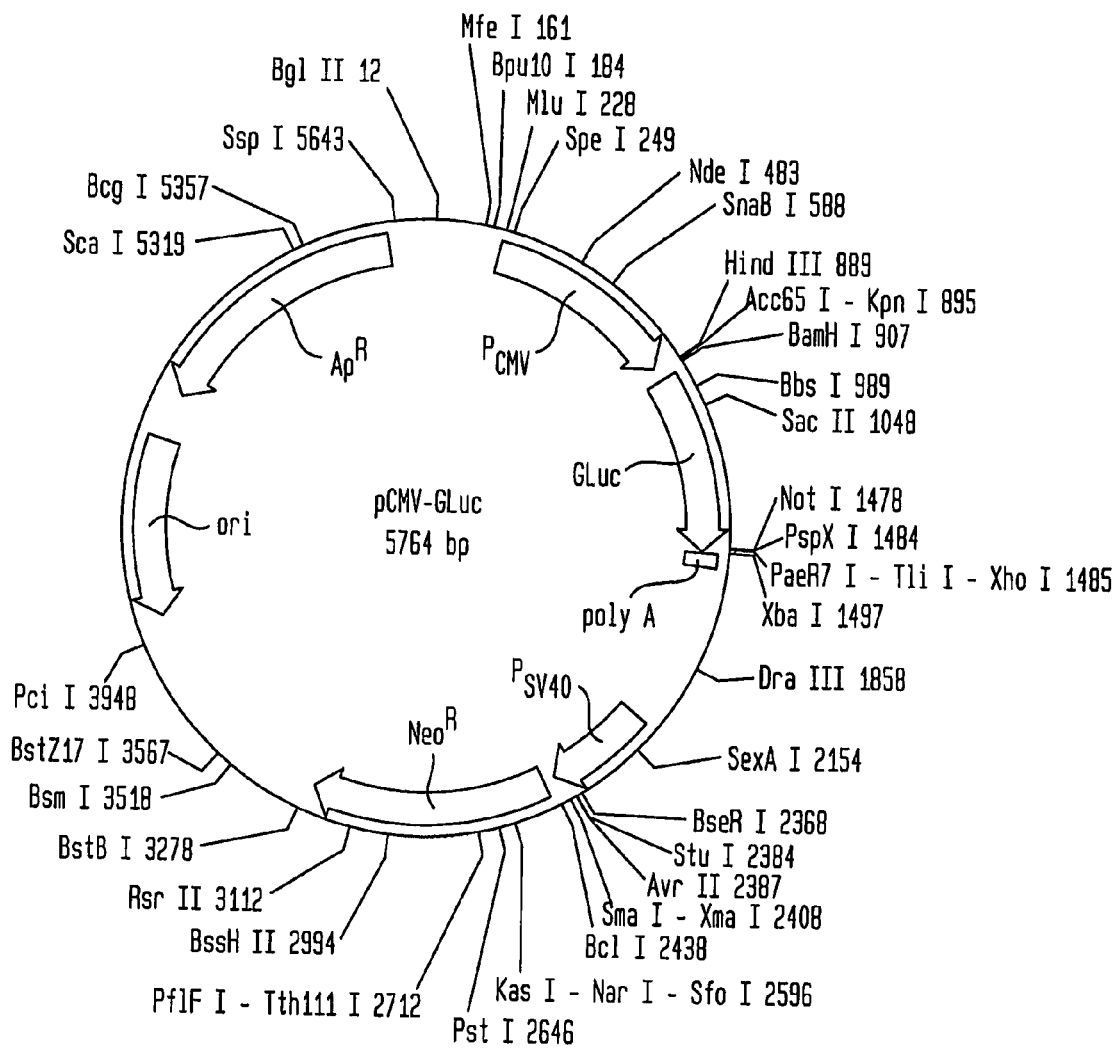

FIG. 18 shows the vector used to transfect mammalian cells with *Gaussia* luciferase.

DETAILED DESCRIPTION

Methods and compositions are described for assaying coelenterazine-dependent luciferase bioluminescence in vitro and in vivo (in cells). The compositions provide at least one of enhanced stability of signal or magnitude of signal by varying the composition of the buffer. One or more of the following parameters have been varied: the presence or absence of EDTA (or CDTA), calcium and magnesium ions; the concentration of NaCl; the concentration of coelenterazine; the effect of ionic and non-ionic detergents, the amount of detergent; how the detergent has been added; and the time over which the signal has been recorded. Also disclosed are dual reporter systems.

Coelenterazine-dependent luciferases (see for example, WO 99/49019) include *Gaussia, Renilla, Pleuromamma*, and *Metridia* luciferases and mutants thereof. Genera that have luciferases that utilize coelenterazine include *Chiroteuthis, Eucleoteuthis, Onychoteuthis, Watasenia*, cuttlefish, *Sepiolina*, and shrimp such as *Oplophorous, Acanthophyra, Sergestes* and *Gnathoplausia*, deep sea fish such as *Agryopelecus, Yarella, Diaphus, Gonadostomias* and *Neoscopelus*. These luciferases vary in their baseline bioluminescence. For example, *Gaussia* luciferase is more than a thousand fold brighter than *Renilla* luciferase when expressed in mammalian cells. However, as shown below, conditions for enhancing the magnitude of the initial bioluminescent signal and then stabilizing it over time for the three exemplified coelenterazine-dependent luciferase—recombinant bacterial *Gaussia* luciferase, *Gaussia* luciferase secreted by mammalian cells and *Renilla* luciferase from cell lysates—are similar despite differences in specific activity. This suggests that these parameters are applicable to coelenterazine-dependent luciferases in general.

Luciferase activity in an assay buffer containing PBS, high salt (for example, 0.5M NaCl) and high coelenterazine molarity (for example, 20 µM) is unstable with 90% of the light production being lost in less than 2 minutes. Stabilizers of the light reaction of non-coelenterazine-dependent luciferases, for example, dithiothreitol (DTT) and Coenzyme A are used with firefly luciferases.

Embodiments of the invention provide a luciferase assay buffer that can generate as much as 10 times greater bioluminescence in both short-term and long-term coelenterazine-dependent luciferase assays when EDTA is omitted from the buffer and the amount of coelenterazine used is increased to as much as 5 µM. This effect is exemplified in Table 3. The effect of various assay conditions on the magnitude and stability of the bioluminescent signal for different luciferases tested is summarized in Table 7. Certain embodiments of the assay buffer provide sustained luminescence over a period of up to at least 45 minutes. Examples of this effect are shown in Table 4 for *Renilla* luciferase and Table 5 for *Gaussia* luciferase.

The examples contain an analysis of *Gaussia* and *Renilla* luciferases but other luciferases can be readily tested and the preferred conditions identified using parameters and assays described herein.

The established practice for assaying coelenterazine-dependent luciferases is to utilize assay buffers that include at least one of EDTA, calcium/magnesium ions, high concentrations of detergent (greater than 1%), high concentrations of salt (0.5M or more) and relatively high levels of coelenterazine (greater than 10 µM) (Tannous et al. *Mol. Therap.* I I(3):435-43 (2005)).

Certain embodiments of the present invention do not require EDTA and establish that calcium and magnesium salts are detrimental for prolonging signal intensity or increasing the magnitude of bioluminescence for coelenterazine dependent luciferases. However, any or all of the following components was found to be beneficial for increasing at least one of magnitude and stability of signal. Low concentrations of NaCl (less than 0.5M), detergents (less than I % v/v) and low concentrations of coelenterazine (10 µM or less) are demonstrated to improve the magnitude of bioluminescence over the short term. Inclusion of EDTA in addition to detergent is helpful to improve stability of the luminescence signal over a time period of greater than 1 minute is required (FIGS. 12-15). In addition, FIG. 15 shows than an improved stability profile is obtained when 1.3 µM coelenterazine is used compared with 4 µM coelenterazine in FIG. 13, particularly for the sample in which detergent is added directly to the luciferase W-

Concentrations of coelenterazine recommended by suppliers (such as Prolume/NanoLight Technologies, Pinetop, Ariz.) significantly exceeded the concentration required for the present embodiments. Benzyl coelenterazine was found to be an effective substrate for *Renilla* luciferase but was not suited as a substrate for *Gaussia* luciferase (see FIGS. 8, 9 and Table 6). Example 2 describes how these different substrate specificities can be used in a dual reporter system.

The effect of varying conditions for bacterial luciferase are illustrated in Tables 2, 6 and 7 and FIGS. 4b and 8, for secreted luciferase from mammalian cells in Tables 1, 3, 5, 6 and 7 and FIGS. 1, 2, 3, 4A, 8, 10-15, 16 and 17 and for *Renilla* luciferase in Tables 3, 4, 6 and 7 and FIGS. 6, 7 and 9.

The effect of increasing NaCl concentration in the assay buffer for *Gaussia* luciferase activity is shown in Table 1 in the absence of NP40 detergent and EDTA and in the presence of NP40 and EDTA. Table 1 shows that increased NaCl in the absence of EDTA reduced bioluminescence but that the presence of EDTA and NP40 reversed this effect. This is opposite to the observations of Shimomurai et al. *Biol. Bull.* 201:339-347 (2001) which reported on the requirement by *Periphylla* for high salt concentration.

The addition of NP40 detergent to the assay reagent at low concentrations (0.5% or less) resulted in a significant increase in luminescent activity for *Gaussia* luciferase and *Renilla* luciferase as well as significant improvement in stability of the luminescent signal compared to assay compositions reported in the literature and those commercially available.

A range of detergents was tested for *Gaussia* luciferase and *Renilla* luciferase (FIGS. 2, 3, 6 and 7). 0.001%-0.5% detergent was found to enhance luminescence. For example, 0.02% detergent was found to be effective in enhancing the magnitude of the bioluminescence within the first 4 minutes after addition of coelenterazine. The improved stabilizing effect was observed over time if the concentration of detergent was increased, for example, to 0.2%.

Low concentrations of detergent, for example, NP40, were shown to stabilize and enhance the luminescent signal with almost no change in the background activity (FIGS. 2, 3, 6 and 7).

Adding detergent directly to a *Gaussia* luciferase preparation prior to adding the assay buffer containing coelenterazine/PBS increased the stability of the signal compared with adding detergent to the assay buffer. Adding the detergent to the assay buffer before use with luciferase increased the magnitude of the initial signal (FIGS. 12-15).

In an embodiment of the invention, coelenterazine was stabilized in acidified dehydrated ethanol and added to the assay buffer at a concentration in the range of I-5 µM. This concentration range was effective for improved *Gaussia* luciferase activity (see FIGS. 4A and 4B). This amount of coelenterazine is substantially less than the minimum of 20 µM previously reported by Tannous et al. *Mol. Therap.* I I(3):435-43 (2005).

In an embodiment of the invention, a kit is provided for assaying a coelenterazine-dependent luciferase. The kit contains an assay buffer and instructions. The kit may be used for example for cell populations, cell lysates and protein solutions.

Manipulation of conditions to alter the magnitude and/or stability of the bioluminescent signal from coelenterazine-dependent luciferases results in products suited for a variety of applications. Applications include: tumor imaging for in vivo visualization of bioluminescent tumors using transfected luciferase or luciferase tagged antibodies; real-time analysis of gene expression; high through-put screening for drug discovery or for screening for gene silencing RNAs; intracellular pathway analysis and immunodiagnostics/enzyme-linked immunosorbent assay (ELISA).

The use of an assay reagent such as described here and in the examples that gives extended bioluminescence over at least a 2-minute period is desirable for such applications. Protein-protein interactions may be monitored using split luciferases. Viability assays involving a coelenterazine-dependent luciferase as a reporter can be used for determining the effectiveness of different drugs in killing bacteria, fungi or viruses and monitoring responses to environmental stress.

Luciferases may be used to identify and quantify oligonucleotide interaction with target DNA sequences. The oligonucleotide of interest would be tagged with luciferase and then exposed to immobilized target DNA on a chip or microtiter dish. Wells containing DNA sequences capable of interacting with the oligo sequence of interest can be visualized using the luciferase. In an embodiment of the invention, *Gaussia* luciferase can be used for any of the above applications. Choice of the assay reagent or buffer for the bioluminescence reaction depends on whether it is preferred to maximize the initial burst of bioluminescence maintaining this for up to 2-4 minutes or whether it is desirable to have a stabilized signal that can be readily detected at 10-15 minutes after addition of luciferase substrate. Accordingly, varying any of the conditions described here such as the addition of 1% EDTA, higher concentrations of detergent such as 0.2% detergent, or higher concentrations of coelenterazine, for example, up to 4-6 µM, may be used to increase stability or increase the amplitude of the initial signal.

A further use of the present assays relates to in vivo experiments to determine gene silencing using siRNA in real time. Secreted *gaussia* luciferase offers advantages over intracellular *Renilla* and Firefly luciferases because bioluminescence can be repeatedly measured and cell lysis is not required.

All of the references, cited above and below, as well as U.S. provisional application No. 60/659,152, are herein incorporated by reference.

EXAMPLES

Example 1

Optimizing the Assay Reagent Composition

*Gaussia* luciferase has been cloned from the copepod, *Gaussia princeps*. (Ballou et al, 11th Symposium on Bioluminescence and Chemiluminescence, Asilomar, Calif. (2000), Verhaegent et al. *Analytical Chemistry* 74:4378-85 (2002), Tannous, et al. *Mol Ther*, II(3):435-43 (2005), Siouxsie Wiles, et al. *Appl. Envir. Microbiol.* 71:3427-3432 (2005), Svetlana *J. Biol. Chem.* 279:3212-32170 (2004)). *Gaussia* luciferase (GLuc, 185 aa, 19.9 kDa) is the smallest luciferase known and is naturally secreted. This luciferase emits light at a peak of 480 nm with a broad emission spectrum extending to 600 nm (Tannous et al. *Mol. Ther*. II(3):435-43 (2005)).

*Renilla* luciferase is commercially available from Prolume/NanoLight Technologies, Pinetop, Ariz. Recombinant bacterial *Gaussia* luciferase was obtained from Prolume/Nanolight Technologies, Pinetop, Ariz.

*Gaussia* luciferase was secreted from mammalian cells after transfection of cells with the vector shown in FIG. 16.

Reagents used in the examples include: PBS (Amresco, Solon, Ohio), PBS with Ca/Mg/K (Invitrogen, Carlsbad, Calif.), Igepal CA-630 referred to throughout as NP40 (Sigma Aldrich, St. Louis, Mo.), Standard *Renilla* assay reagent (Promega, Madison, Wis.), coelenterazine and benzyl coelenterazzine (Prolume/NanoLight Technologies, Pinetop, Ariz.), expression vector for *Gaussia* luciferase in mammals (New England Biolabs, Inc., Ipswich, Mass.), Dulbecco's minimal essential medium (DMEM) (Invitrogen, Carlsbad, Calif.) used for diluting mammalian and bacterial expressed *Gaussia* luciferase. Measurements of bioluminescence were carried out with a luminometer (Turner TD2020 luminometer, Turner BioSystems, Sunnyvale, Calif.).

Formulation of Standard *Gaussia* Assay Reagent

Stock solutions of the following were used in the preparation of various assay buffers: A stock solution of 10×PBS was obtained commercially from AMRESCO, Solon, Ohio. A stock solution of 2% EDTA was prepared by dissolving 2 grams of EDTA in water to a final volume of 100 ml.

Stock solutions containing 2% detergents: 2% v/v stock solutions of NP40, Triton X-100, Tween8O and DOC were prepared by adding 2 ml of the detergent solution to 98 ml of water. A stock solution of 2% SDS was prepared by dissolving 2 gms of SDS in water and bringing up the final volume to 100 ml.

Stock solutions containing 0.2% detergents were prepared by a 1:10 dilution of the 2% stock solutions in water.

Assay buffers containing PBS, EDTA and detergents were prepared by diluting appropriate amounts of the stock solutions in water to give the desired final concentrations of PBS, EDTA or detergent.

Coelenterazine or benzyl coelenterazine was dissolved in acidified dehydrated ethanol as follows: 3 mg coelenterazine was mixed with 1 ml absolute ethanol and 25 µl 2N HCL. Ethanol was added in a ratio of 4:1 (i.e., 4 ml of ethanol to 1 ml of coelenterazine in acidified ethanol) to prepare a 100× concentrated stock solution of coelenterazine or benzyl coelenterazine. An amount of this coelenterazine solution was added to the assay buffer to a final concentration in the range of I-10 µM. 50 µl of the assay buffer was mixed with 20 µl of sample containing luciferase and bioluminescence was measured using a luminometer.

Identification of Conditions for Improved Magnitude and/or Maintenance of Signal from Coelenterazine-Dependent Luciferases.

1. Determination of the Effect of Calcium/Magnesium and or EDTA on the Magnitude of the Signal from *Gaussia* Luciferase:

An amount of powdered bacterial *Gaussia* luciferase obtained from Nanolight Technologies, Pinetop, Ariz., was dissolved in DMEM and diluted in control assay buffer until a reading could be obtained from a luminometer. The results shown in FIG. 1 utilize assay buffers consisting of 0.5×PBS, 0.5×PBS/Ca/Mg, 0.5×PBS/1 % EDTA, and 0.5×PBS/Ca/Mg/1 % EDTA, each buffer further including 1.3 µM coelenterazine. The best results were obtained here with PBS alone in addition to the coelenterazine with a signal that was about 5 times greater then in the presence of either or both of calcium, magnesium or EDTA.

Figure 1:
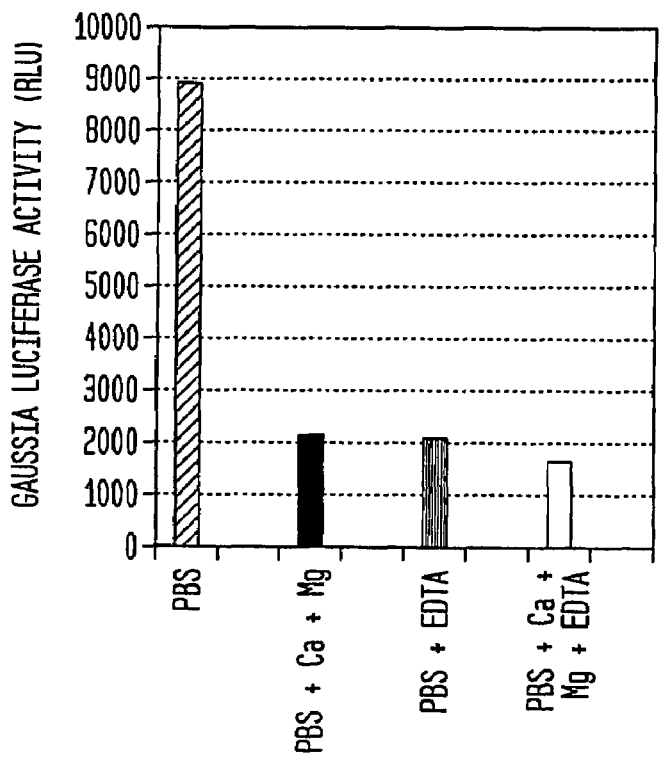
FIG. 1 shows the effect of different buffer composition on the activity of *Gaussia* luciferase secreted from mammalian cells where phosphate-buffered saline (PBS) alone generates a significantly greater signal than when calcium, magnesium, or/and EDTA are added with the PBS.
Figure 2:
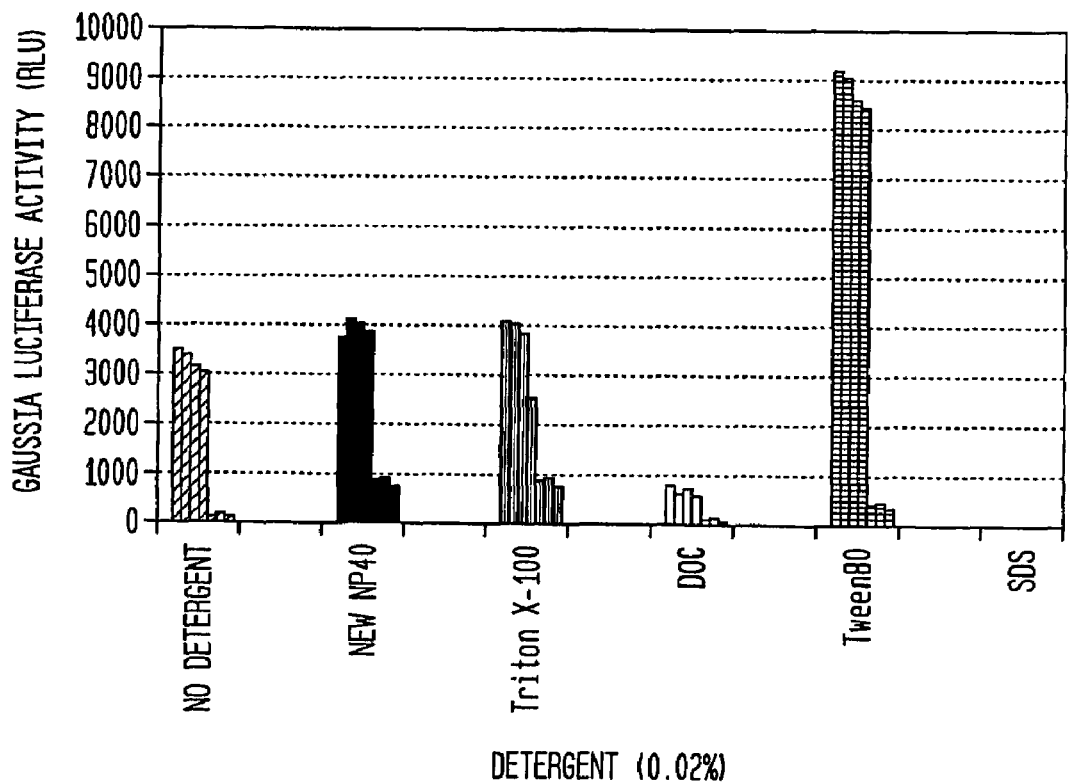

2. Determination of the Effects of Different Detergents at a Concentration of 0.02% V/V in the Assay Reagent on *Gaussia* Luciferase Activity and *Renilla* Luciferase Activity In this example, 20 µl of mammalian *Gaussia* luciferase samples (cell supernatants) were mixed with 8 µl of the indicated detergents at 2% and 0.2% concentration (final concentration of detergents in assay solution was 0.2% and 0.02%) and 50 µl of the *Gaussia* luciferase assay reagent (0.5×PBS, no EDTA, 1.3 µM coelenterazine) and read in a Turner TD2020 Luminometer, Turner BioSystems, Sunnyvale, Calif. The samples were read again after 15 minutes to evaluate the stability of the luminescent signal in the presence of different detergents. The results using different detergents are shown in FIGS. 2, 3 and Table 6 (for *Gaussia* luciferase) and FIG. 6 for *Renilla* luciferase. For both *Gaussia* and *Renilla* luciferases, optimum stability was observed using NP40 and Triton X-IOO.

3. Determination of the Effects of Different Concentrations of Coelenterazine in the Assay Reagent on Mammalian-Secreted *Gaussia* Luciferase Activity and Recombinant Bacterial *Gaussia* Luciferase (FIGS. 4A and 4B)

Purified mammalian-secreted *Gaussia* luciferase was tested in an assay reagent of 0.5×PBS plus 1% EDTA, 0.2% NP40 and 1.3 µM, 4 µM, 6 µM, 12 µM and 25 µM (FIG. 4A) or 1.3 µM, 3.8 µM, 4 µM, 6 µM, 12 µM and 25 µM coelenterazine.

The effect of two different concentrations of coelenterazine (1.3 µM and 4 µM) were further investigated in assay reagents where the presence or absence of 1% EDTA and the use of 0.2% or 0.02% NP40 was also tested for *Gaussia* and *Renilla* luciferases (Table 3). Table 4 shows the effect of different concentrations of NP40 and coelenterzine in the absence of EDTA for time periods of 0, 7, 20 and 80 minutes 4. Substitution of Coelenterazine with Benzyl Coelenterazine

*Gaussia* luciferase responds poorly to the use of Benzyl coelenterazine as a substrate (see Table 3). However, *Renilla* luciferase produces a significantly enhanced signal with benzyl coelenterazine and the signal is relatively stable compared to that using coelenterazine as a substrate (FIG. 9 and Table 6).

5. Effect of Varying Concentrations of NaCl in the Assay Reagent

The effect of varying concentrations of NaCl in an assay reagent consisting of 0.5×PBS and 1.3 µM coelenterazine-depressed bioluminescence at concentrations exceeding about 0.5M NaCl. This effect was not significant when 0.025% NP40 and 1% EDTA were also present (Table 1).

6. Effect of adding EDTA to the assay reagent on magnitude and stability of the bioluminescent signal is shown in Table 2 and FIGS. 12-15. 1% EDTA had the effect of depressing the initial magnitude of the signal but produced a more stable profile of bioluminescence over time.

The effect of varying the amount of NP40 (0.02% or 0.2%) added directly to the luciferase or added into the assay reagent, the presence or absence of EDTA, the amount of coelenterazine (4 µM or 1.3 µM) over 0-120 seconds and 0-about 1000 seconds is summarized in FIGS. 10-15 and Table 7 for mammalian-secreted *Gaussia* luciferase. Table 7 also summarizes the effect of varying conditions according to the above for *Renilla* luciferase and bacterial *Gaussia* luciferase.

TABLE 1

Effect of salt concentration (NaCl) in the assay buffer on bioluminescence from mammalian-secreted Gaussia luciferase at zero time

| NaCl concentration in adjusted 0.5 × PBS + 1.3 µM coel. | RLU | NaCl concentration in adjusted 0.5 × PBS + 1% EDTA + 0.025% NP40 + 1.3 µM coel. | RLU |
|---|---|---|---|
| .075M NaCl | 2866 | 0.075M NaCl | 1041 |
| | 2322 | | 1145 |
| | 1746 | | 1110 |
| | | 0.175M NaCl | 1322 |
| | | | 1350 |
| | | | 1242 |
| | | 0.275M NaCl | 1364 |
| | | | 1252 |
| | | | 1204 |
| | | 0.375M NaCl | 1129 |
| | | | 1098 |
| | | | 1246 |
| 0.5M NaCl | | 0.575M NaCl | 1049 |
| | 1212 | | 1035 |
| | 701 | | 1149 |
| 1M NaCl | 760 | | |
| | 750 | | |

TABLE 2

Effect of adding EDTA in the assay buffer on magnitude and stability of the bioluminescence from purified recombinant bacterial Gaussia luciferase at two different time points (minutes)

| Buffer: 0.5 × PBS, 0.025% NP40 and 1.3 µM coel. | RLU at T = 0 | RLU at T = 5 |
|---|---|---|
| +1% EDTA | 800 | 71 |
| | 730 | 66 |
| | 892 | 72 |
| −1% EDTA | 1643 | 310 |
| | 1558 | 306 |
| | 1586 | 321 |

TABLE 3

Effect of EDTA, different concentrations of NP40 and different concentrations of coelenterazine on bioluminescent magnitude and stability (time is in minutes.)

|  | Gaussia Luciferase (Bacterial) | | Gaussia Luciferase (Mammalian) | | Renilla Luciferase | |
|---|---|---|---|---|---|---|
|  | T = 0 | T = 10 | T = 0 | T = 10 | T = 0 | T = 20 |
| 0.5xPBS, 0.025% NP40, 1.3 μM coel., +1% EDTA | 1630 | 58 | 594 | 31 | 2296 | 194 |
|  | 1837 | 59 | 565 | 30 | 1780 | 139 |
|  | 1903 | 60 | 556 | 29 | 2520 | 211 |
| 0.5xPBS, 0.025% NP40, 1.3 μM coel., −1% EDTA | 8508 | 165 | 2696 | 94 | 5562 | 2047 |
|  | 9008 | 181 | 2717 | 95 | 5540 | 1958 |
|  | 9153 | 179 | 2502 | 96 | 5260 | 2016 |
| 0.5XPBS, 0.025% NP40 + 4 μM coel., −1% EDTA | 15000 |  | 4907 | 297 | 20000 | 3421 |
|  | 15000 |  | 5364 | 313 | 20000 | 3676 |
|  | 15000 |  | 4612 | 304 | 20000 | 3912 |
| 0.5xPBS, 0.2% NP40 + 4 μM coel., −1% EDTA | 3469 |  | 1399 | 175 | 10555 |  |
|  | 3455 |  | 1453 | 182 | 10111 |  |
|  | 3302 |  | 1493 | 184 | 10393 |  |

TABLE 4

Effect of different concentrations of NP40 and coelenterazine on stabilization of Renilla luciferase signal (time in minutes)

|  | T = 0 | T = 7 | T = 20 | T = 80 |
|---|---|---|---|---|
| 0.5 × PBS | 716 | 136 | 27 | 8 |
|  | 753 | 149 | 28 | 9 |
|  | 670 | 116 | 23 | 7 |
| 0.5 × PBS, 0.2% NP40, 4 μM coel. | 943 | 753 | 513 | 256 |
|  | 959 | 777 | 526 | 259 |
|  | 895 | 699 | 480 | 237 |
| 0.5 × PBS, 0.025% NP40, 4 μM coel. | 3716 | 2030 | 1494 | 441 |
|  | 3950 | 2130 | 1553 | 443 |
|  | 4093 | 2164 | 1598 | 489 |

TABLE 5

Effect of 0.2% detergent final concentration in buffer containing 0.5xPBS, 1% EDTA, 1.3 μM coelenterazine on bioluminescence from Gaussia luciferase (mammalian) (time in minutes and bioluminescence in RLU)

|  | T = 0 | T = 15 | T = 45 |
|---|---|---|---|
| no detergent | 1629 | 38 | 20 |
| NP40 | 87 | 112 | 79 |
| Triton X-100 | 59 | 80 | 63 |
| DOC | 4 | 2 | 2 |
| Tween80 | 128 | 101 | 58 |
| SDS | 0 | 0 | 0 |

TABLE 6

Effect of using 1.3 μM benzyl coelenterazine instead of 1.3 μM coelenterazine in the assay buffer (0.5xPBS, 0.025% NP40) at two different time points (minutes)

|  | Gaussia luciferase (bacterial) | | Gaussia luciferase (mammalian) | | Renilla luciferase | |
|---|---|---|---|---|---|---|
|  | t = 0 | t = 10 | t = 0 | t = 10 | t = 0 | t = 20 |
| Coel. | 1630 | 58 | 594 | 31 | 2296 | 194 |
|  | 1837 | 59 | 565 | 30 | 1790 | 139 |
|  | 1903 | 60 | 556 | 29 | 2520 | 211 |
| Benzyl Coel. | 81.75 | 7.9 | 34 | 3.49 | 9036 | 2234 |
|  | 83 | 8.1 | 30 | 3.6 | 7687 | 1944 |
|  | 84 | 8.1 | 31 | 3.66 | 7955 | 1359 |

TABLE 7

Summary of effect on magnitude (M at t = 1-2 minutes) and stability (S at time = 7-10 minutes) of bioluminescent signal from coelenterazine-dependent luciferases

|  | NaCl conc. 0.075M compared to 0.5M | 1% EDTA compared to 0% | 0.2% NP40 compared to 0.025% or 0% | 4 μM coel. compared to 1.3 μM | 4 μM benzyl coel. compared to 1.3 μM |
|---|---|---|---|---|---|
| bacterial Gluc |  | M down | S up | M up | M down |
|  |  |  | M down |  | S down |
| Mammalian Gluc | M down −EDTA−NP40 M same + EDTA | S up M down | S up M down | M up | M down S down |

TABLE 7-continued

Summary of effect on magnitude (M at t = 1-2 minutes) and stability (S at time = 7-10 minutes) of bioluminescent signal from coelenterazine-dependent luciferases

| | NaCl conc. 0.075M compared to 0.5M | 1% EDTA compared to 0% | 0.2% NP40 compared to 0.025% or 0% | 4 µM coel. compared to 1.3 µM | 4 µM benzyl coel. compared to 1.3 µM |
|---|---|---|---|---|---|
| Bacterial | | | S up | M up | M up |
| Rluc | | S down | M down | S down | S up |
| Firefly | | M down | S up | | |
| | | M down | | | |

Example 2

Dual Reporter System

1. A Dual Reporter System Using *Renilla* and *Gaussia* Luciferase is Described Here.

This system relies on the differential effect of the substrate benzyl coelenterazine shown in Table 6 and FIGS. 8 and 9 on the activities of *Renilla* and *Gaussia* luciferases. The effect can be further exploited because *Gaussia* luciferase is secreted from mammalian cells while *Renilla* luciferase is not (see FIG. 15). FIG. 15 shows that 96.2% of *Gaussia* luciferase is secreted into the supernatant medium and only about 3.8% is cell-associated. Accordingly, multiple gene expression systems can be measured simultaneously using both *Gaussia* luciferase and *Renilla* luciferase as reporters. Accordingly, the DNA encoding these luciferases can be introduced into a population of mammalian cells by co-transfection. The amounts of intracellular *Renilla* luciferase can be determined using benzyl coelenterazine as the substrate while the amount of secreted *Gaussia* luciferase activity can be determined using coelenterazine as a substrate. Because coelenterazine is a substrate for both *Gaussia* and *Renilla* luciferase, quantitation of the *Gaussia* luciferase can be determined by subtracting the bioluminescence using coelenterazine from the value obtained using benzyl coelenterazine.

An assay reagent (0.4×PBS, 0.025% NP40, 1.3 µM coelenterazine) was used to evaluate *Gaussia* luciferase activity in cell supernatants of transfected human embryonic kidney (HEK-293) cells over 8 days (see FIG. 12). At the end of the time course experiment, if the group of cells is also transfected with plasmid DNA expressing *Renilla* luciferase which is not secreted, the cells can be lysed and assayed using 0.5×PBS, 0.2% NP-40, 4 uM Benzyl coelenterazine.

An advantage of the dual reporter system described here over a firefly luciferase/*Renilla* luciferase reporter system is that time-course or drug-response experiments can be performed on the same group of transfected cells (by assaying *Gaussia* luciferase activity in the supernatant) without the need for cell lysis at every time point. At the end of the experiment, the cells can be lysed and the cell lysates assayed for *renilla* luciferase activity.

2. A Dual Luciferase Assay Based on Firefly and *Gaussia* Luciferase

95% of *Gaussia* luciferase was secreted into the supernatant medium and only about 5% was cell-associated (FIG. 15). The activity of a gene of interest can be studied using *Gaussia* luciferase as a reporter. Normalization of transfection efficiency is accomplished by co-transfection with an expression vector expressing firefly luciferase. A dual assay reagent is formulated for simultaneous analysis of cell-associated firefly luciferase activity (using firefly luciferin as the substrate) and secreted *Gaussia* luciferase activity (using coelenterazine as a substrate) (see Table 7).

An advantage of the proposed dual luciferase assay system over the firefly luciferase/*Renilla* luciferase reporter systems presently used is that time course or drug response experiments can be performed on the same group of transfected cells (by assaying *Gaussia* luciferase activity in the supernatant) without the need for cell lysis at every time point. At the end of the experiment, the cells can be lysed and the cell lysates assayed for firefly luciferase activity.

3. A Dual Reporter System in a Viable Cell Preparation Utilizing, for Example, *Gaussia* Luciferase and *Vargula* Luciferase (WO 99/49019)

A live cell dual assay for simultaneous analysis of gene expression from two different promoters has been developed by transfecting cells with two different plasmid vectors, one vector expressing *Gaussia* luciferase and the second vector expressing *Vargula* luciferase under control of a different promoter. Promoter activity of the construct expressing *Gaussia* luciferase can be studied using the assay buffer composition described above to measure *Gaussia* luciferase activity in the cell supernatants at different time intervals without lysing the cells.

Promoter activity of the second promoter (expressing *Vargula* luciferase) can be studied by assaying cell supernatants with an assay buffer (identical to the composition described for assay of gaussia luciferase but containing cypridina luciferin (the substrate for *Vargula* luciferase) in place of coelenterazine.

Example 3

Direct Detection of Cells Expressing Luciferase

HEK-293 cells were transfected with the *Gaussia* luciferase vector according to FIG. 18 using standard tissue culture techniques. After forming a cell monolayer, 10 or 50 µl of assay containing 0.5×PBS, 0.025% NP40, 0.02% NP40 and 1.3 µM or 4 µM coelenterazine was added to IOO µl of DMEM and 10% fetal bovine serum and cells in wells of a 96 well dish. Transfected cells glowed according to the buffer conditions consistent with Example 1 and could be identified with the naked eye. This assay is expected to work for any coelenterazine-dependent luciferase transfected tissue culture cells.

What is claimed is:

1. A luciferase assay buffer, comprising: coelenterazine, sodium chloride at a concentration less than in physiological saline, and a detergent, wherein the detergent concentration is in a concentration of less than 1%, the assay reagent being suitable for measuring bioluminescence of a coelenterazine-dependent luciferase for a time in excess of at least 30 seconds for *Gaussia* luciferase and 1 minute for *Renilla* luciferase by means of a luminometer.

2. A luciferase assay buffer according to claim 1, suitable for measuring bioluminescence for at least 30 seconds from *Plurimamma* luciferase and *Metridia* luciferase.

3. A luciferase assay buffer according to claim 1, wherein the sodium chloride has a concentration in the range of 0.01-0.15M.

4. A luciferase assay buffer according to claim 3, such that the buffer contains substantially no calcium or magnesium ions.

5. A luciferase assay buffer according to claim 1, wherein the buffer optionally contains EDTA at a concentration of no more than 3%.

6. A luciferase assay buffer according to claim 1 further comprising a non-ionic detergent at a concentration in the range of 0.01%-0.5%.

7. A luciferase assay buffer according to claim 6, wherein the detergent is selected from the group consisting of: Igepal CA-630 (NP40), Triton X-100, Tween8O and deoxycholate (DOC).

8. A luciferase assay buffer according to claim 1, wherein the colenterazine is present in the buffer at a concentration of no greater than 5 µM.

9. A luciferase assay buffer according to claim 1, wherein the luciferase is selected from *Gaussia, Renilla, Pleuromamma* and *Metridia* luciferase.

10. A luciferase assay buffer according to claim 1, wherein the luciferase is *Gaussia* luciferase.

11. A luciferase assay buffer according to claim 1 or 4, wherein the salt concentration is in the range of about 0.01-0.15M, the coelenterazine is at a concentration of less than about 5 µM and the buffer further contains a non-ionic detergent at a concentration in the range of about 0.01%-0.5%.

12. A luciferase assay buffer according to claim 1, wherein the coelenterazine concentration is 1 µM-5 µM, the non-ionic detergent is at a concentration of at least 0.05% and the buffer further comprises EDTA, wherein the assay buffer is capable of stabilizing the bioluminescent emission of *Gaussia* luciferase for longer than 2 minutes.

13. A luciferase assay buffer according to claim 1, wherein the non-ionic detergent has a concentration of less than 0.1%, the assay buffer being capable of enhancing the amount of bioluminescence for *Gaussia* luciferase for a time period of at least 30 seconds in the absence of EDTA.

14. A kit comprising a luciferase assay buffer according to claim 1, and instructions.

15. A method for measuring bioluminescence from a coelenterazine-dependent luciferase, comprising selecting an assay buffer according to claim 1, and adding the assay buffer to the luciferase.

16. A method according to claim 15, wherein the concentration of detergent is between 0.001% and 0.5%, and the assay buffer optionally contains EDTA at a concentration no greater than 3%.

17. A method according to claim 15, wherein the coelenterazine has a concentration of less than about 5 µM.

18. A method of enhancing bioluminescence from a coelenterazine-dependent luciferase reaction, comprising: selecting an assay buffer according to claim 13, and adding the assay buffer to the luciferase.

19. A method of stabilizing a bioluminescent signal from a coelenterazine-dependent luciferase reaction, comprising adding an assay buffer of claim 12 to a preparation of coelenterazine-dependent luciferase.

20. A method according to claim 18 or 19, wherein the concentration of coelenterazine is less than about 5 µM.

21. A method for direct detection of a cell transformed with a gene encoding *Gaussia* luciferase, comprising: adding an assay buffer according to claim 1 to the cell in a culture medium, and detecting bioluminescence by microplate luminometer or microscopy.

22. A method for detection of a cell transformed with a gene encoding *Gaussia* luciferase, said method comprising adding a luciferase buffer to said cell in a culture medium and detecting bioluminescence by microplate luminometer or microscopy, wherein said luciferase buffer comprises coelenterazine, sodium chloride at a concentration less than in physiological saline, and a detergent, wherein the detergent concentration is in a concentration of less than 1% and wherein the *Gaussia* luciferase gene is fused with a gene expressing a target protein and the fusion gene is co-transformed with a gene expressing an siRNA for gene silencing.

23. A method according to claim 1, wherein the concentration of coelenterazine is about 25 µM.

24. A kit comprising a luciferase assay buffer according to claim 11, and instructions.

* * * * *